United States Patent [19]

Banker et al.

[11] Patent Number: 5,643,730

[45] Date of Patent: Jul. 1, 1997

[54] PROCESS FOR DETECTING SPECIFIC MRNA AND DNA IN CELLS

[75] Inventors: Michael J. Banker, Groton; Ralph E. Davidson, North Stonington; Dennis A. Pereira, Stonington, all of Conn.

[73] Assignee: Pfizer Inc., New York, N.Y.

[21] Appl. No.: 403,555

[22] Filed: Mar. 14, 1995

Related U.S. Application Data

[63] Continuation of Ser. No. 52,805, Apr. 23, 1993, abandoned, which is a continuation of Ser. No. 764,462, Sep. 23, 1991, abandoned.

[51] Int. Cl.$^6$ .............................. C12Q 1/68; C12Q 1/70; C12P 19/34; C07H 21/04
[52] U.S. Cl. .......................... 435/6; 435/5; 435/91.2; 435/174; 435/183; 536/24.3; 536/24.32; 536/24.33
[58] Field of Search .............. 435/5, 6, 91.217, 435/174, 183; 536/24.3, 24.33

[56] References Cited

U.S. PATENT DOCUMENTS

| | | | |
|---|---|---|---|
| 4,358,586 | 11/1982 | Rubin | 536/27 |
| 4,483,920 | 11/1984 | Gillespie et al. | 435/6 |
| 4,683,195 | 7/1987 | Mullis et al. | 435/6 |
| 4,683,202 | 7/1987 | Mullis | 435/91 |
| 4,800,159 | 1/1989 | Mullis et al. | 435/172.3 |
| 4,851,331 | 7/1989 | Vary et al. | 435/6 |
| 5,231,015 | 7/1993 | Cummins et al. | 435/91 |
| 5,334,499 | 8/1994 | Burdick et al. | 435/6 |

FOREIGN PATENT DOCUMENTS

| | | |
|---|---|---|
| 2016518 | 11/1990 | Canada . |
| 1291429 | 10/1991 | Canada . |
| 164876 | 12/1985 | European Pat. Off. . |
| 326395 | 8/1989 | European Pat. Off. . |
| 329822 | 8/1989 | European Pat. Off. . |
| 370813 | 5/1990 | European Pat. Off. . |
| 303844 | 10/1990 | European Pat. Off. . |
| 395292 | 10/1990 | European Pat. Off. . |
| 428197 | 5/1991 | European Pat. Off. . |
| 2187283 | 9/1987 | United Kingdom . |
| 8808038 | 10/1988 | WIPO . |
| 8810315 | 12/1988 | WIPO . |
| 8901050 | 2/1989 | WIPO . |
| 8909285 | 10/1989 | WIPO . |
| 9001065 | 2/1990 | WIPO . |
| 9001069 | 2/1990 | WIPO . |
| WO90/02821 | 3/1990 | WIPO . |
| 9008456 | 8/1990 | WIPO . |
| 9009456 | 8/1990 | WIPO . |
| 9102817 | 3/1991 | WIPO . |
| 9105064 | 4/1991 | WIPO . |

OTHER PUBLICATIONS

Voller, A., et al., *The Enzyme Linked Immunosorbent Assays* (Elisa) (1979), 1SBN 0–906036.01.1, pp. 7–43.
Elrich, H. A., Ed., *PCR Technology*, M. Stockton Press (1989), Chps 1–4, 8, 9, 14–16, 18 and 19.
Ausubel, F.M. et al., Eds., *Current Protocols in Molecular Biology*, Greene Publishing Associates and Wiley–Interscience (1987), Chapters 4 and 9.
Ferre, F. et al., Nucleic Acids Research 17:2141 (1989).
Forest, C. et al., Experimental Cell Research, 168:218–232 (1987).
Gill, P. et al., Nature 318:577–579 (1985).
Kogan, S.C. et al., N. E. J. Med. 317:985–990 (1987).
Li, H. et al., Nature 335:414–417 (1988).
Maniatis et al., *Molecular Cloning A Laboratory Manual*, Cold Spring Harbor Lab., 1982, p. 89.
Saiki, R.K. et al. Science 230:1350–1354 (1985).
Saiki, R.K. et al. Science 239:487–491 (1988).
Patel et al. "Sequence Analysis and Amplification by Polymerase Chain Reaction of a Cloned DNA Fragment for Identification of Mycobacterium Tuberculosis" J. of Clinical Microbiology, 28: 513–518, Mar. 1990.
Ferre and Garduno, "Preparation of Crude Cell Extract Suitable for Amplification of RNA by the Polymerase Chain Reaction" Nar 17: 2141, 1989.
Li et al. "Amplification and Analysis of DNA Sequences in Single Human Sperm and Diploid Cells" Nature 355:414417, 1988.

*Primary Examiner*—W. Gary Jones
*Assistant Examiner*—Dianne Rees
*Attorney, Agent, or Firm*—Peter C. Richardson; Gregg C. Benson

[57] ABSTRACT

This invention relates to a process for detecting the presence and measuring the quantity of specific mRNA sequences present in in vivo cells or cells maintained in vitro. The process of this invention is applicable to the screening of procaryotic and eucaryotic organisms including the screening of human beings for the presence of disease states. The process of this invention is also applicable to the in vitro screening of the effect or effects of chemical compounds upon one or several gene products as exhibited by the presence and amount of mRNA resulting from transcription of said gene or genes. The process of this invention is particularly suited for screening of a large number of compounds for the effect or effects of compounds upon gene products. This invention also relates to compounds capable of affecting the presence of specific mRNA sequences in cells. The process of this invention also is applicable to the identification of novel gene constructs in viruses, microorganisms, plants and animals. This invention also relates to a novel process for the isolation of RNA and DNA from cells.

22 Claims, No Drawings

PROCESS FOR DETECTING SPECIFIC MRNA AND DNA IN CELLS

CROSS REFERENCE TO RELATED APPLICATION

This application is a continuation of application Ser. No. 08/052.805, filed Apr. 23, 1993, now abandoned., which is a continuation of application Ser. No. 07/764,462, filed Sep. 23, 1991, now abandoned.

TECHNICAL FIELD

This invention relates to a process for detecting the presence and measuring the quantity of specific mRNA sequences present in in vivo cells or cells maintained in vitro. The process of this invention is applicable to the screening of procaryotic and eucaryotic organisms including the screening of human beings for the presence of disease states. The process of this invention is also applicable to the in vitro screening of the effect or effects of chemical compounds upon one or several gene products as exhibited by the presence and amount of mRNA resulting from transcription of said gene or genes. The process of this invention is particularly suited for screening of a large number of compounds for the effect or effects of compounds upon gene products. Further, this invention relates to compounds capable of affecting the presence of specific mRNA sequences in cells.

Further still, the process of this invention is applicable to the identification of novel gene constructs in viruses, microorganisms, plants and animals. This invention also relates to a novel process for the isolation of RNA and DNA from cells.

BACKGROUND ART

Enzymatically amplified antibody assays have been successfully used to specifically monitor the expression of protein gene products in 96 well microtiter dish formats. See The Enzyme Linked Immunosorbent Assays (ELISA), Voller, A., Bidwell, D. E. and Bartlett, A. (1979) ISBN 0-906036.01.1. However, attempts to similarly monitor mRNA gene products in a 96 well microtiter format have failed due to the lack of sensitivity of the methods employed and the lack of facile mRNA isolation procedure. *Current Protocols in Molecular Biology*, F. M. Ausubel, R. Brent, R. E. Kingston, D. D. Moore, J. G. Seidman, J. A. Smith and K. Struhl, EDS., Greene Publishing Associates and Wiley-Interscience (1987). Further, the up and/or down regulation of a particular gene can be indirectly measured by reporter gene constructs which rely on the heterologous expression of a gene product that is capable of subsequent detection. *Current Protocols in Molecular Biology*, Supra. While the latter approach is useful, it suffers from several limitations. Those limitations include the need to prepare, identify and characterize appropriate constructs; the constructs comprise a heterologous promoter and a reporter gene which necessitates that the promoter be available and characterized; promoter activity only is measured; use of enzymes to measure activity means that translation and/or enzyme inhibitors can compromise the integrity of the assay; and integration of the reporter gene may not be targeted to the natural chromosomal site and often times multiple copies per cell result which can influence gene regulation.

A method which utilizes gene specific oligomers to provide specificity for a particular gene and particular DNA polymerases to amplify the specific gene sequences to detectable levels, a method generally known as polymerase chain reaction or PCR, is described by Saiki, R., et al., Science 230: 1350 (1985) and Saiki, R. K., et al., Science 239: 487 (1988).

It has been reported that mRNA could be detected from cells cultivated in vitro in a well of a 96 well microtiter dish. Russell Higuchi, Simple and Rapid Preparation of Samples for PCR in *PCR Technology*, Henry A. Elrich, Ed., M. Stockton Press (1989). However, the mRNA isolation method employed therein is not conducive to the utilization of PCR in screening processes, particularly when such screening involves a plurality of samples.

DISCLOSURE OF THE INVENTION

This invention concerns a novel process for the detection and measurement of specific mRNA and DNA sequences in cells. Further, this invention concerns a novel process for providing RNA and DNA from cells. The cells employed in the processes of this invention can be taken directly from an in vivo source or maintained in vitro. The specific mRNA sequence or sequences detected by the processes of this invention is not limited to any class or type of mRNA. The processes described herein are applicable to any mRNA species provided it is possible to produce cDNA therefrom.

The novel process of this invention for detection and measurement of specific mRNA sequences in cells comprises the steps of removing the biological fluid or culture medium, as the case may be, from the cells; lysing the cells by adding water to the cells in a vessel and maintaining the vessel in a liquid of a temperature from about 90° C. to about 115° for about two to about twelve minutes to produce a lysate; permitting the lysate to cool; producing a cDNA sequence from one or a plurality of mRNA sequences present in the lysate; amplifying the number of copies of the cDNA sequence or sequences; detecting the presence of the cDNA sequence or sequences and, if desired, measuring the quantity thereof. Optionally and preferably, the cells are washed with an isotonic solution which is them removed from the cells prior to lysis. Further, optionally and preferably, the lysate containing the cDNA sequence is treated with proteinase prior to amplification. A prefered proteinase is proteinase K. It is further preferable to lyse the cells by maintaining the vessel containing the cells in a liquid of a temperature at about 99° C. for about four to about eight minutes with a period of about six minutes being particularly preferred.

The novel process of this invention for detection of specific DNA in cells comprises removing the biological fluid or culture medium, as the case may be, from the cells; lysing the cells by adding water to the cells in a vessel and maintaining the vessel in a liquid of a temperature from about 90° C. to about 115° C. for about two to about twelve minutes to produce a lysate; permitting the lysate to cool; amplifying the number of copies of the DNA sequence of interest; and detecting the presence of the DNA sequence. As above, it is optional and preferable to wash the cells with an isotonic solution and remove the solution prior to lysis. It also is preferable to lyse the cells by maintaining the vessel containing the cells in a liquid of a temperature at about 99° C. for about four to about eight minutes with a period of about six minutes being particularly preferred.

The novel process for the isolation of RNA and DNA which is employed in the above described process comprises lysing cells from which the RNA and DNA is desired by adding water to the cells in a vessel and maintaining the vessel in a liquid of a temperature from about 90° C. to about 115° C. for about two to about twelve minutes with a temperature at about 99° C. and a period of about four to about eight minutes being preferred. A period of about six minutes is particularly preferred. The lysate which is produced contains cell debris and the contents of the cytoplasm including the RNA and DNA present therein.

The novel processes of this invention provide for the facile production of nucleic acid which can be amplified by a variety of methods known to those skilled in the art. One such method is that known as polymerase chain reaction or PCR technology.

Because the processes herein described are so facile, many samples of different cells or cells treated differently can be assayed according to the processes of this invention in order to detect and, where desired, quantitate specific mRNA sequences within those cells. The processes of this invention find particular utility in the screening of the effect or effects of compounds upon the presence of specific mRNA sequences of the cells. Thus, the processes of this invention are well suited to the drug discovery process and can result in high throughput screening of large numbers of compounds. Thus, this invention also relates to compounds, identified according to the process of this invention, which affect the presence of specific mRNA sequences in cells.

Using the processes of this invention it is possible to assay more than one mRNA sequences at a time. For example, hybridization for G-CSF and GM-CSF sequences can be done simultaneously with kinased probes since increase G- or GM-CSF mRNA levels are desired in both cases. If desired, the individual products could be measured individually by using oligomer probes varying in detection method (e.g., radioisotope vs. fluorescence and/or radioioisotopes having varying specific activity). Further, it is possible to wash and reprobe. It is also possible to divide the amplified material between two or among three or more nylon membranes as a method to increase the number of multiplexed products being measured, or as a method to enhance detection of specific products.

The novel processes of this invention are not limited, however, to utility in such high throughput screens. The processes of this invention are useful for the identification of chimeric organisms including viruses, microorganisms, animals and plants wherein one or more foreign genes have been introduced. Thus the identity and stability of such chimeric organisms can be assayed through the use of the processes of this invention. Further, it is possible, with the invention processes hereof, to determine gene structure and integration of genes through the study of co-amplified genes or portions thereof.

The processes of this invention are also useful as clinical and diagnostic methods. The processes herein enable one to detect the presence of specific mRNA associated with particular disease states. For example, the highly sensitive processes provided by the present invention enable the detection of certain mRNA associated with cancer during the period of latency before metastasis. Hence, by employing the processes hereof in such a manner, treatment can commence at an early stage in the development of the cancer. By way of further example, the presence of mRNA associated with active infection in a person suffering from AIDS can be detected according to the processes of this invention. Thus, it is possible to diagnose active AIDS patients.

DETAILED DESCRIPTION

Appropriate buffers and reagents for use in the practice of this invention are as follows:

20X Reverse Transcriptase/Taq Polymerase Buffer
1M Tris-Cl, pH 8.3
1M KCl
80 mM $MgCl_2$
Annealing/RT Buffer (per well)
8.13 µl sterile distilled water
1.00 µl 10X Reverse Transcriptase/Taq Polymerase Buffer
0.64 µl 25 mM dNTP (25 mM dATP, 25 mM dTTP, 25 mM dGTP and 25 mM dCTP)
0.09 µl 1M dithiothreitol
0.04 µl to 0.08 µl X primer at 1 µg/µl
0.01 µl RNasin (50 U/µl)
0.01 µl AMV reverse transcriptase (32U/µl)
PCR Reagents (per 10 µl addition)
8.68 µl sterile distilled water
1.0 µl 10X Reverse Transcriptase/Taq Polymerase Buffer
0.04 µl to 0.08 µl X primer at 1 µg/µl
0.20 µl Taq Polymerase (5 U/µl)
Dot Blot DNA Denaturing Solution
444 mM NaOH (160 ml 500 mM NaOH)
11 mM EDTA (8 ml 250 mM EDTA)
0.00074% Ink (16 µl of 10% India ink)
22 ml distilled water
1M $Na_2 HPO_4$ pH 7.2 (1M in $Na^+$)
134 g $Na_2 HP \cdot 7H_2O$
4 ml 85% $H_3PO_4$
Bring to 1 liter with $H_2O$
Hybridization Buffer
7% SDS
5X SSC
20 mM $NaPO_4$
10X Denhardt's Solution
Hybridization Wash Solution
1% SDS
1X SSC
20X SSC
3M NaCl (175 g/L)
0.3M Sodium citrate $\cdot 2H_2O$ (88 g/L)
Adjust pH to 7.0 with 1M HCl
100X Denhardt's Solution
2% Ficoll 400
2% polyvinylpyrrolidone
2% bovine serum albumin (Pentax fraction V)
10X Kinase Buffer
500 mM Tris-Cl, pH 7.4
100 mM $MgCl_2$
50 mM DTT The enzymes of the above reagents are commercially available. For example RNasin can be obtained from Boehringer Mannheim, AMV reverse transcriptase can be obtained from Molecular Genetics Inc., and Taq Polymerase can be obtained from Perkin Elmer. All of the other components of the above buffers and reagents are also commercially available. Further, it is preferable to sterilize the stock solutions.

The cells employed in the processes of this invention can be isolated from an animal or plant and used directly in the processes described herein below. Alternatively, and preferably when conducting high throughput screens, the cells are cultured under appropriate conditions prior to use in the processes of this invention. As used throughout this specification and the appendant claims, the term animal includes, but is not limited to mammals such as human beings. The cells of this invention are not limited to eukaryotic cells but include prokaryotic cells as well.

The cells can be cultured in a variety of vessels, for example, in microtiter dishes or microtiter tubes according to well known methods. Microtiter dishes are commercially available with 6, 24, 48, 96 or 144 wells. Use of microtiter dishes is preferable for application of the processes of this invention to high throughput screening. While the cells can be cultured in other appropriate vessels such as roller bottles or petri dishes, such vessels are not as suitable due to their size and associated handling problems. The processes of this invention are not limited in any way, however, to the method and/or apparatus by or in which the cells are cultured. Commercial sources of microtiter dishes include Costar, Falcon, Nunc and Corning.

One such method for cultivating eukaryotic cells for use in the processes of this invention comprises seeding an appropriate number of cells in the desired number of wells of microtiter dishes or microtiter tubes. The optimal number of cells for seeding is determined by the person practicing this invention and will vary depending upon the type of cell and the target of the assay. Such determination merely requires application of the processes described below to a series of cultures of the cell type to be assayed, which cultures have been seeded with increasing numbers of cells. The determination is thus well within the skill of those who practice in the relevant art, enabled by this disclosure. For example, it has been found that $1 \times 10^4$ trypsinized cells per well of 96 well microtiter dish is an appropriate number of seed cells when employing murine or human fibroblasts and assaying for granulocyte-macrophage-colony stimulating factor (GM-CSF), granulocyte-colony stimulating factor (G-CSF) and/or aldolase mRNA according to the process of this invention described below.

The seeded cells are then allowed to proliferate for an appropriate period of time. The period of time for such proliferation will vary with the type of cell that was seeded and the conditions under which the cells are proliferated. One skilled in the art will readily determine an appropriate period of time for such proliferation bearing in mind that the desired result of such proliferation is the obtention of a sufficient number of cells at an appropriate physiological state to carry on the subsequent steps of the method of this invention as described hereinbelow. By an appropriate physiological state it is meant that the cells are in a state such that they are susceptible to modulation of the target mRNA specie or species. For example, an appropriate period for proliferation of murine or human fibroblast cells has been found to be two days. Such cells are incubated at 37° C. in the presence of about 6-7% $CO_2$.

Following appropriate proliferation, the cells can be assayed for the presence of specific mRNA or can be further treated with one or more test compounds prior to such assays. If it is desired to test one or more compounds for the effect thereof upon the level of one or more mRNA in the cells, then the compound or compounds under study are added to the cells. It has been found that it is preferable to add the compound under study so that a final concentration of about 5 µg/ml is achieved. This can be obtained by adding 10% of the final volume of a solution containing about 50 µg/ml of the compound. If a plurality of microtiter dishes are being used, it is preferable to add compounds to the dishes in groups of four dishes so that temperature shock to the cells can be reduced. Appropriate controls are included in each dish. For example, to designated wells are added 10% of the final volume (e.g. 20 µl) of 1 mM Tris, pH 7.3. For certain tests, positive controls can also be included wherein a known inducer of the mRNA under study is added to designated wells.

After the additions to the wells have been made as described above, the dishes are incubated for an additional period of time. The period of additional incubation will vary to a greater or lesser extent depending upon the cells used and the mRNA species being assayed. The optimum period of additional incubation can be readily determined by one skilled in the art based upon the disclosure herein. For example, when using human fibroblast cells in an assay to determine the effect of compounds on the ability of those cells to express mRNA for granulocyte-macrophage colony stimulating factor, granulocyte-colony stimulating factor and/or aldolase, it is preferable to incubate the dishes for an additional 90–180 minutes in a $CO_2$ incubator (37° C., 6–7% $CO_2$). It is also preferable to process the dishes in the same groups of four so that all dishes are incubated for about the same period of time.

Following the additional incubation described above, the dishes are removed from the incubator and quickly inverted to remove the culture medium. Then, the dishes are inserted into a microplate washer such as a Bio-Rad Microplate Washer (Bio-Rad Catalog No. 170-6540) and rinsed with 37° C. prewarmed Phosphate Buffered Saline (PBS), such as Hazelton Dulbecco's Phosphate Saline, Cat. No. 310–4190AK, using three cycles of rinse/aspirate with about 200 µl per cycle. The aspirate height is adjusted to leave about 100 µl of PBS in each well of the dishes at the end of each wash cycle. The remaining PBS is then removed by vigorously inverting the dishes. Then, the dishes are blotted using a flat absorbent material such as a paper towel being careful not to blot the inside of the wells.

After the dishes are blotted, as described above, 50 µl of room temperature distilled water are added to each well of the dishes. As described above, when working with a plurality of dishes it is preferable to process the dishes in groups of four. To add 50 µl of water to the dishes, it is preferable to employ a multiple tip pipetter such as a Soken Sigma Pet 96 Pippetter (Soken Tokyo, Japan) and to process groups of four dishes at one minute intervals. Immediately following addition of the water, the dishes are floated on a mineral oil bath to lyse the cells. The temperature of the mineral oil can be from about 90° C. to about 115° C. with about 99° C. being preferred. The dishes are maintained in the mineral oil bath for about two to about twelve minutes with about four to about eight minutes being preferred and about six minutes being particulary preferred. Then, 10–12 µl of the lysate are aspirated from each well, preferably using a second multiple tip pipetter such as one of the type described immediately above. Preferably, the lysate (10–12 µl) is allowed to cool in the Soken tips for about 5 to about 15 seconds with about 7 seconds being particularly preferred, and then immediately transferred to vinyl dishes having the same number and configuration of wells and containing 10 µl/well of cold Annealing/RT Buffer. Alternatively, the lysate can be cooled in the vessel for about one to two minutes. It is to be noted that the Annealing/RT Buffer is unstable. Therefore, it is preferable to prepare the Annealing/RT Buffer, less the reverse transcriptase and primer or primers, immediately prior to commencement of the assay and to divide the Buffer into aliquots sufficient for use in about 30 dishes. Then, immediately prior to adding the Annealing/RT Buffer to the dishes, the reverse transcriptase and primer or primers are added to one of the aliquots of Buffer, keeping the Buffer cold. As more Annealing/RT Buffer is needed, reverse transcriptase and primer or primers are added to additional aliquots of the Buffer. The second multiple tip pipetter may be rinsed with sterile water before use to transfer lysate from the next dish.

It is preferable to prechill the dishes and keep the dishes cold by floating them on a water/ice slurry. Immediately following addition of the Annealing/RT Buffer, the vinyl dishes are transferred to a programmable thermal controller ("PTC") such as an M-J Research Programmable Thermal Controller (96 well configuration, M-J Research, Watertown, Mass.) which has had its wells filled to about one-third of their volume with mineral oil. The PTC is preprogrammed to incubate the dishes at 42° C. for 15 minutes before rising to 95° C. for 5 minutes. After completing the heating cycle, the vinyl dishes are cooled to 4° C. It is preferable, particularly when practicing the process of this invention with multiple small volume samples, to not overlay the wells with mineral oil during the heating cycle.

To each well of the dishes are added 10 µl Proteinase K (500 µg/ml) and then 50 µl of mineral oil are overlayed in each well. Here, too, it is preferable to use a multiple tip pipetter such as one of the type described above. The dishes are then placed in a PCT which is programmed to heat to 60° C. for 10 minutes followed by 95° C. for 10 minutes. After completing the heating cycle, the plates are cooled to 4° C. until proceeding to the next step.

To each well of the dishes are added 10 µl of PCR Reagent solution, preferably with a multiple tip pipetter such as one of the type described above. The dishes are then transferred to a PTC that is preprogrammed for 31 cycles of 92° C. for 90 seconds followed by 60° C. for 120 seconds followed by 72° C. for 180 seconds. After the cycles are completed, the PTC is programmed to cool to 4° C. As would be well known to those skilled in the art enabled by the disclosure herein, other times, temperatures and number of cycles are possible and are within the scope of this invention.

The method can be used with multiple sets of oligomers such that more than one target sequence can be simultaneously amplified. Often one member of the multiple is used as a control, the only prerequisites are primer compatibility and compatible kinetics of induction, repression or mRNA half life. While any set of oligomer pairs can be used, provided that the amplified product is long enough to provide an unique DNA sequence for subsequent probing/ quantitation, it is preferred to keep the size of the amplified product less than about 300 bp to maximize the efficiency of the PCR reaction. Two methods are available, which methods utilize the exon intron relationship to minimize or prevent artifactual quantitation of genomic DNA. A first method comprises selecting oligomer pairs which are separated by intron(s) whose extent or sum exceed about 500 bp. The increase in length of the amplified product reduces the efficiency of the PCR amplification and reduces or eliminates the amplification of the genomic DNA while leaving the mRNA dependent PCR amplified unaffected. A second method comprises selecting oligomers wherein the last few (2 or 3) bases of each of the oligomers are homologous to the adjacent exon. This allows for amplification of mRNA but does not allow for the amplification of the intron since the oligomer lacks homology on its 3 prime end, preventing the intron from being copied.

While it is preferable to use nonlabeled or nondistinct nucleotides in the PCR Reagent solution, it is possible to include appropriately radiolabeled or otherwise detectable nucleotides in the PCR Reagent solution. Of course, any such nucleotide must not affect the amplification of the desired sequence. If such radiolabeled or other detectable nucleotides are used during amplification of the sequence, then the presence of the sequence is measured by methods appropriate to the label or detectable nucleotide. Such methods are well known to those skilled in the art and include dot blot autoradiography and enzyme linked anti-avidin/biotin detection. If, as is preferable, amplification of the sequence is not carried out in the presence of radiolabeled or otherwise detectable nucleotides, then it is preferable to detect the presence of the amplified sequence or sequences by hybridization with an appropriate probe as described below. While the probe described below is radiolabeled, other suitable probes which are capable of detection and measurement by such methods as chemiluminescence, fluorescence, acridinium esters or enzyme linked anti-avidin/biotin detection can be used. Methods to produce such probes are well known to those skilled in the art enabled by the disclosure herein.

To each well of the dishes are added 50 µl of distilled water, once again preferably with a multiple-tip pipetter such as one of the type described above. Then, 50 µl of the solution which contains the amplified PCR product or products are withdrawn from each well and delivered into microtubes, such as 1.2 ml microtubes, each containing 250 µl of Dot Blot Denaturing Buffer. It is preferable to place the microtubes in a rack which does not contain a bottom which could affect the subsequent heating of the tubes. The tubes are placed in water at or above 95° C. for five minutes. The resulting solution of denatured DNA can then be stored at room temperature or higher for a limited time before proceeding to the next step.

To appropriate nylon membranes that have been soaked for at least one minute in water are added 250 µl from each microtube containing denatured DNA prepared as described above. It is preferable that the nylon membrane be a ZETA-PROBE™ nylon membrane (Bio-Probe, Catalog No. 162-0153) and that the membrane not be touched by unprotected hands. Further, it is preferable that the membranes be placed in a Dot Blot apparatus (Bio-Rad, Catalog No. 170-6545), the vacuum be turned on to remove excess water prior to addition of the denatured DNA solution and that a Soken pipetter be used to add the denatured DNA solution to the membrane. Further still, the membranes should be numbered and indexed so that correlation can be made between the membranes and the original dishes. Once the denatured DNA solution has been added to the membranes, it is preferable to apply vacuum and continue until dry. The membranes are then removed from the apparatus and briefly rinsed in 2X SSC followed by air drying on filter paper.

A probe for screening the membranes is prepared as follows. In an appropriate vessel, such as a 0.5 ml Eppendorf tube, a reaction mixture is prepared by adding the following components in the order listed:

1. 10X Kinase Buffer 5 µl
2. Sterile distilled water 32 µl
3. Oligomer (1 µg/µl) 1 µl
4. Gamma $^{32}$P-ATP (10 µCi/µl) 10 µl.

The mixture is heated to 65° C. for 10 minutes, then quickly cooled in ice whereupon kinase (8 U/µl, 1 µl) is added. A preferred kinase is T4 Kinase which is commercially available. Following addition of kinase, the reaction is incubated at 37° C. for 30 minutes. The reaction is then stopped by heating at about 95° C. for 5 minutes. It is possible to monitor percent incorporation of label by sampling before and after incubation at 37° C. and counting total and TCA precipitable counts per minute. Of course, all of the operations involving the use of radioisotope are performed with care using gloves and appropriate shielding. The oligomer probe used will vary depending upon the species of mRNA under study. The oligomer used can also be a combination of oligomers having various lengths and/or coding sequences. The oligomer or oligomers are prepared using standard DNA synthetic techniques well known to those skilled in the art to which this invention pertains or purchased commercially (e.g., Genosys, Tex.). It is preferable to select oligomers which contain about 50% of their sequence homologous to an adjacent exon or exons to insure that the probe quantitates mRNA rather than genomic DNA.

The membranes which have been prepared as described above are placed in sealable pouches or bags with about 75 ml of Hybridization Buffer. It is preferable to use a plastic food bag such as DAISY™ USA. The bags are sealed and immersed in a 37° C. shaking water bath for at least 20 minutes. Then, the bags are opened slightly and 1 µl of 95° C. treated probe (about $1 \times 10^7$ cpm/µg oligomer) is added to each bag. The bags are resealed, after excess air has been massaged out, and immersed in a shaking water bath for hybridization. The temperature of the water bath for hybridization will vary as a function of the probe and mRNA species under study. The temperature for such hybridization is readily determined by one skilled in the art enabled by the disclosure herein. Hybridization is conducted for at least 4 hours. However, it is preferable to permit hybridization to continue overnight.

After hybridization, the bags are opened and the hybridization solution is carefully poured into an appropriate vessel or vessels, such as 50 ml tubes, for proper storage and disposal. The membranes, still in the bags or plastic container with a lid, are rinsed with about 200 ml of Hybridization Wash Solution, the wash solution is poured off and about 200 ml of fresh Hybridization Wash Solution are added to each. The bags or plastic containers are resealed and placed in a shaking water bath for about 30 minutes. The temperature of the water bath at this point is also a function of the probe and mRNA species and is also readily determined by one skilled in the art enabled by the disclosure herein. The bags or plastic containers are then opened and the Hybridization Wash Buffer poured off. Then, a small amount of Hybridization Wash Buffer is added to each bag, the membranes are rinsed therewith and the Hybridization Wash Buffer is discarded. To each bag or plastic container is added 200 ml of fresh Hybridization Wash Buffer, the bags are resealed and placed in a shaking water bath for about 30 minutes at the same temperature used for the wash described immediately above. The process of rinsing and washing is repeated yet once or twice more. Then, the membranes are removed from the bags or plastic containers and placed on sheets of filter paper to air dry.

The dried membranes are then counted using an appropriate device. For example, when using a 96 well dish format in the method of this invention, it is preferable to use a Matrix 96 Counter (Packard, A Canberra Co., Conn.).

The data are collected and analyzed in the following manner:

1) Either specific wells which did not receive test reagent are used for controls or, in the case of tests which have few values which diverge from that of the controls, data from all positions are collected and the median value is used as a control;
2) Each experimental value is divided by the control value;
3) Values are considered to be divergent from that of the controls according to those criteria that are set by the person performing the process of this invention.

Values greater than and less than the control can be discerned by this method.

In practicing this invention in a high throughput screen, it is preferable to employ an appropriate computer program to analyze the data in accordance with the above described procedure. Such programs can be readily written by those skilled in the art to run on mainframe or personal computers. Further, commercially available software such as Lotus or Excel Spreadsheets can be used to analyze and present such data.

The procedure described above is also applicable to cells obtained directly from an in vivo source. For example, tumor or tissue cells can be obtained from the source by aseptic excision or other appropriate methods (e.g., buccal scraping). An example of the practice of this invention with murine tumor cells is described below.

Murine tumor cells obtained by asceptic excision, are placed into a 10 cm dish, covered, weighed and minced in 1 ml of a collagenase solution containing 2 mg/ml collagenase, 2% bovine serum albumin and 4 mM L-glutamine, pH 7.4. Then, the cells are trypsinized in a flask containing one part collagenase solution, as described above, and two parts of Dulbecco's Modified Eagle Medium (DMEM) supplemented with 10% fetal calf serum (FCS), 0.6% L-glutamine, 10 units/ml penicillin/streptomycin, 0.25 µg/ml fungizone, 17 µM calcium pantothenate, 33 µl d-biotin, 100 µM ascorbic acid and 0.82 mM $Na_2CO_3$. The flasks are covered with aluminum foil and incubated in a rotary shaker at 140 rpm for 60 minutes at 37° C. During the incubation the cell suspension is gently pipetted every 15 minutes to dispense tissue fragments and break up clumped cells, with 10 µl of DNase (2450 Units/ml) per ml of cell suspension being added after 15 minutes of incubation. The cell suspension then is passed through a 100 micron mesh nylon screen with the volume increased four fold using supplemented DMEM described above. The cells are centrifuged at 800 xg for 10 minutes at 4° C., the supernatant is decanted and the cells resuspended in 0° C. supplemented DMEM. Centrifugation is repeated for a total of 10 times and the cells are finally suspended in supplemented DMEM (4 ml per gram of cells) at 0° C. The cell suspension is then passed through a 40 micron mesh nylon screen.

At this point the cells can be washed with phosphate buffered saline, then lysed and the desired sequence amplified and analyzed as described above. Alternatively, the cells can be plated directly into multiple well dishes and used according to the method described above. Alternatively still, the cell viability can be determined using standard methods well known to those skilled in the art, such as trypan blue dye exclusion. The cells are then seeded at a density of $1 \times 10^7$ cells per 10 cm tissue culture plate. The cells are grown to confluency, scraped from the tissue culture dish and resuspended in 10 ml of supplemented DMEM. A 1 ml cell suspension is pelleted in a 1.5 ml Eppendorf tube, the pellet is washed once with phosphate buffered saline and pelleted again. The cells are then lysed in 250 µl of water as described above. Then, 50 µl of the lysate is used with 50 µl of the desired reverse transcriptase reaction mixture followed by amplification and detection of the desired sequences, all as described above.

As used throughout the specification and appendant claims, the singular tense includes the plural tense and vice-versa. While the foregoing description discloses the process of this invention employing the use of plurality of microtiter dishes, the process of this invention is equally applicable to any other vessel type and number of samples. By way of example and not of limitation, the process can be used with one microtiter dish, a plurality of tubes or even a single tube. The procedures described above for the process of this invention are applicable mutatis mutandis to such other vessels. Further, the volumes given herein are approximate and are not to be viewed as limiting the invention. As long as the appropriate ratios of volumes and quantities used are maintained, total volumes and quantities employed may be varied up or down without departing from the scope of this invention. All references to $H_2O$ or water throughout this specification and the appended claims, unless specifically noted otherwise, are to deionized $H_2O$ or water.

EXAMPLE 1

Screening for Effect of Compounds on Granulocyte-Macrophage Colony Stimulating Factor (GM-CSF) mRNA Levels, Aldolase mRNA Levels and Granulocyte Colony Stimulating Factor (G-CSF) mRNA Levels in Muman Fibroblasts 1a. Establishment of Primary Fibroblast Cell Line Human foreskin tissue sourced locally was minced and treated with collagenase (1 mg/ml, 37° C., in 10–20% heat inactivated (56° C., one-half hour) fetal calf serum (FCS)). The cells were maintained in tissue culture at 37° C. with 7% $CO_2$ in Dulbecco's Modified Eagle Medium (DMEM) (Hazelton DME media, Cat. #51-43378) supplemented with 10% FCS, and 10 units/ml of penicillin and 10 µg/ml of streptomycin (P/S). The cells were grown near confluency in tissue culture flasks. Then, the cells were trypsinized (0.25% trypsin, 0.02% EDTA) and diluted 1 to 4 in DMEM plus 10% FCS and P/S. The cells were then returned to the $CO_2$ incubator (7% $CO_2$). The process of trypsinizing and growing the cells was repeated until a sufficient number of cells were obtain. It was found that three to five repetitions usually provided a sufficient number of cells. The cells were then suspended in DMEM supplemented with 25% fetal calf serum and 10% dimethylsulfoxide at about $5 \times 10^6$ cells/ml. Following the addition of dimethylsulfoxide, the cells were immediately separated into 1 ml aliquots and stored in liquid nitrogen.

1b. propagation of Fibroblasts

A frozen aliquot of fibroblasts, prepared as described in 1a, above, was rapidly thawed by immersion in a 37° C. water bath. The thawed cells were transferred to a 175 cm² flask containing 50 ml of DMEM supplemented with 10% FCS and P/S. Once established, the cells were trypsinized as described in 1a, above, every three to four days or when the cells reached confluency. The cells were so maintained for up to 12 passages.

1c. Seeding of Microtiter Dishes

Two days prior to the assay, the fibroblasts, prepared according to 1b, above, were removed from the flasks by trypsinization according to the procedure described in 1a, above. The cells were diluted in DMEM supplemented with 10% FCS and P/S to a cell density of about $5 \times 10^4$ cells/mi. Then, 200 µl of the diluted cells were added to each well of flat bottom 96 well microtiter dishes. The dishes were incubated at 37° C. and 7% $CO_2$ for about 48 hours.

1d. Addition of and Incubation with Compounds Under Study

Compounds to be studied were prepared at a concentration of about 50 µg/ml in 1 mM Tris pH 7.3 and 0.9% DMSO, and 20 µl (10% of final volume) were added to two or three wells/compound. No more than about four dishes at a time were removed from the incubator to add compounds thereto. This minimized temperature shock to the cells. As controls, to a first designated well was added 10 ng (20 µl) of murine IL-1 alpha (mIL-1, prepared at Pfizer Inc by known recombinant DNA techniques and expressed in *E. coli*), to a second designated well was added 1 ng (20 µg) of mIL-1, to a third designated well was added 0.1 ng (20 µl) of mIL-1 and to three additionally designated wells were added 20 µl per well of 1 mM Tris (pH 7.3). The dishes were incubated for about 180 minutes at 37° C. in a $CO_2$ incubator (7% $CO_2$). In order to maintain about 180 minute incubation for a series of wells, groups of wells were processed in about 5 minute intervals.

1e. Recovery of the Cells

The dishes, in groups of 3 to 6 were removed from the incubator. As soon as possible, the plates were quickly inverted to remove the culture media, inserted into a Bio-Rad microplate Washer (Bio-Rad Cat. #170-6540) and rinsed with prewarmed (37° C.) PBS (Hazelton Dulbecco's Phosphate—Buffered Saline, Cat. #310-4190AK) using the microplate washer with three cycles of rinse/aspirate at 200 µl per cycle. The aspirate height was adjusted so that, at the end of each cycle, about 100 µl of PBS remained in each well. After the wash, the remaining PBS was removed from the wells by vigorously inverting the dishes and blotting the inverted dishes onto a flat paper towel taking care not to blot the inside of the wells.

1f. Lysis of Cells and Amplification of DNA Sequence

Working in groups of four dishes at one minute intervals, 50 µl of room temperature distilled water were added to each well using a Soken Sigma Pet 96 Pippetter. Immediately following the addition of water, the dishes were floated on a 99° C. mineral oil bath for six minutes. Then, using another Soken Sigma Pet 96 Pippetter, 10–12 µl of the lysate from each well were removed and cooled for 7 seconds in the tips. Then the lysate was transferred to 96 well vinyl dishes (Costar Serocluster "U" Vinyl Plates, Cat. #2797) containing 10 µl/well of cold Annealing/RT Buffer which dishes were resting on an ice slurry. The Annealing/RT Buffer contained 0.08 µl of primer SEQ ID NO: 1 (5'CTTGTAGTGGCTGGCCATCATGGTCAA, 1 µg/µl) to anneal to GM-CSF mRNA, 0.04 µl of primer SEQ ID NO: 2 (5'GTGAGCGATGTCAGACAGCTCC, 1 µg/µl) to anneal to aldolase mRNA and 0.08 µl of primer SEQ ID NO: 3 (5'GAAAGCAGAGGCGAAGGCCGGCAT, 1 µg/µl) to anneal to G-CSF mRNA, the AMV reverse transcriptase was obtained from Molecular Genetics Inc. (Cat. #310-4190AK) and the RNasin was obtained from Boehringer Mannhelm (Cat. #799-025). The dishes were immediately transferred to an M-J Research Programmable Thermal Controller-96 well configuration with each well about one-third full with mineral oil and which was programmed to incubate the dishes at 42° C. for 15 minutes before rising to 95° C. for 5 minutes. Then, the dishes were cooled to 4° C. To each well were added 10µl of Proteinase K (500 µg/ml) Boehringer Mannhelm, Cat. #1092-766) and then 50 µl of light mineral oil (Fisher Chemical Cat. #0-121-1), were overlayed by the Soken pipetter. The dishes were then placed in an M-J Research Programmable Thermal Controller programmed to heat to 60° C. for 10 minutes before indexing to 95° C. for 10 minutes. The plates were then cooled to 4° C.

To each well of the dishes were added to 10 µl of PCR Reagent solution using a Soken pipetter. The PCR Reagent solution contained 0.08 µl of primer SEQ ID NO: 4 (5'GGCACTGTGGCCTGCAGCATCTCT, 1 µg/µl) to amplify the GM-CSF sequences, 0.04 µl of SEQ ID NO: 5 (5'CGCAGAAGGGGTCCTGGTGA, 1 µg/µl) to amplify the aldolase sequences and 0.04 µl of SEQ ID NO: 6

(5'TTTGCCACCACCATCTGGCAGCAG, 1 µg/µl) to amplify the G-CSF sequences and the Taq Polymerase was obtained from Perkin-Elmer (AMPLI-TAQ™ Polymerase, Cat. #N801-0060). The dishes were transferred to an M-J Research Programmable Thermal Controller that was programmed for 31 cycles of 92° C. for 90 seconds followed by 60° C. for 120 seconds followed by 72° C. for 180 seconds. The controller was also programmed to cool the dishes to 4° C. after the thirty-first cycle.

1g. Detection of the Amplified DNA Sequence

To each well of the dishes treated as described in 1f, above, were added 50 µl of sterile distilled water using a Soken pipetter. Then, using a Soken pipetter, 50 µl were withdrawn from each well and delivered into 1.2 ml microtubes containing 250 µl of DOT BLOT™ Denaturing Buffer. The tubes were positioned in a rack from which the bottom had been removed. The rack was placed in a water bath at or above 95° C. for 5 minutes. Then, 250 µl were removed with a Soken pipetter and delivered to a Bio-Rad DOT BLOT™ Apparatus (Cat. #170-6545) containing a Bio-Rad ZETA-PROBE™ Nylon Filter (Cat. #162-0153) that had been soaked in water for a minute or longer and to which vacuum had been applied to removed excess water. The Bio-Rad Zeta-Probe Nylon Filters were handled with glove protected hands and the filters were numbered and indexed with a pen. After blotting, vacuum was applied and continued until all wells were dry.

The filters were removed from the apparatus and briefly rinsed with 2X SSC followed by air drying on filter paper. The filters were then placed in sealable plastic bags to which were added about 75 ml of Hybridization Buffer. The bags were sealed and immersed in 37° C. shaking water bath for at least 20 minutes. The bags were then opened slightly and 1 µg of 95° C. treated probe (about 1×10$^7$ cpm/µg of each oligomer probe of SEQ ID NO: 7 (5'GCAGGTCGGCTCCTGGAGGTCAAACAT) to detect GM-CSF sequences, SEQ ID NO: 8 (5'CTGGCACAGGAGAGGGGCGGGTG) to detect aldolase sequences and SEQ ID NO: 9 (5'TTCCCAGTTCTTCCATCTGCTGCCAGATGG) to detect G-CSF sequences) was added to each. The bags were resealed after excess air had been massaged out of the bags. The bags were immersed in a 37° C. shaking water bath for at least 4 hours. Then, the hybridization solution was carefully poured into 50 ml tubes for storage and disposal.

The filters were each rinsed with about 200 ml of Hybridization Wash Solution, the wash solution was removed and about 200 ml of fresh Hybridization Wash Solution were added. The bags were resealed and placed in a 52° C. shaking water bath for 30 minutes.

The process of rinsing and washing was repeated once or twice for each filter.

After the last rinse and wash, the filters were removed from the bag and transferred to filter paper sheets to air dry. When dry, the filters were counted using a Matrix 96 Counter.

The resulting data from the Matrix 96 Counter was collected and formatted on a personal computer for transfer to a VAX mainframe computer. The data was analyzed as described above using a software program written to run on a VAX mainframe computer.

Using the procedure described in this Example 1, it was possible to screen a large number of compounds during one week for their ability to affect the level of mRNA encoding GM-CSF, aldolase and/or G-CSF.

EXAMPLE 2

Allele Typing of the Human LDLr Gene

Buccal cells were collected by scraping the inside of an individual cheek with a toothpick. The cells were suspended in 200 µl of 95° C. H$_2$O in a 0.5 ml Eppendorf tube and boiled for four minutes. After the tube was quick cooled on ice, 8 µl of 10 mg/ml proteinase K was added and the sample was incubated at 60° C. for 20 minutes. The lysate was then heat inactivated at 95° C. for 10 minutes. Then, 50 µl of the lysate was added to 50 µl of PCR Reagent solution which consisted of 41.5 µl H$_2$O, 5.5 µl 20x PCR buffer, 2 µl of 25 mM dNTPs, 0.5 µl Taq polymerase (Perkin-Elmer), 0.25 µl of primer SEQ ID NO: 10 and SEQ ID NO: 11 (5'AGTGCCAACCGCCTCACAGG and 5'CCTCTCACACCAGTTCACTC, each at 1 µg/µl). The LDLr gene fragment was then amplified through 30 PCR cycles consisting of 1.5 minutes at 95° C., 2 minutes at 60° C. and three minutes at 72° C. The amplified DNA was then dot blotted as described in Example 1 and probed with allele specific radioactive oligomers SEQ ID NO: 12 or SEQ ID NO: 13 (5'AGGATATGGTCCTCTTCCA or 5'TGGAAGAGAACCATATCCT). Bound probe was subsequently quantitated using a Beta scope blot analyzer (Betagert).

What is claimed is:

1. A method for detecting the presence of specific mRNA in cells which comprises the steps of:
   (a) removing the culture medium or biological fluid in which the cells are cultured or exist;
   (b) lysing the cells by adding deionized or distilled water to the cells in a vessel and maintaining the vessel in a liquid of a temperature from about 90° C. to about 115° C. for about two to about twelve minutes to produce a lysate;
   (c) permitting the lysate to cool;
   (d) producing one or more cDNA sequences from mRNA of a specific sequence or specific sequences present in and not separated from the lysate;
   (e) amplifying the number of copies of the cDNA sequence or sequences; and
   (f) detecting the presence of the cDNA sequence or sequences.

2. The method according to claim 1 wherein, in step (f), detecting the presence of the cDNA sequence or sequences comprises quantitating the amount of the cDNA sequence or sequences.

3. The method according to claim 1 which comprises the additional step of washing the cells with an isotonic solution and removing the solution from the cells prior to step (b).

4. The method according to claim 1 wherein, in step(b), the vessel is maintained in a liquid of a temperature at about 99° C. for about four to about eight minutes.

5. The method according to claim 1 which comprises the additional steps of heating the cDNA sequences and then treating the cDNA sequences with proteinase prior to step (e).

6. The method according to claim 2 which comprises the additional steps of heating the cDNA sequences and then treating the cDNA sequences with proteinase prior to step (e).

7. The method according to claim 3 which comprises the additional steps of heating the cDNA sequences and then treating the cDNA sequences with proteinase prior to step (e).

8. The method according to claim 7 wherein, in step (b), the vessel is maintained in a liquid of a temperature at about 99° C. for about six minutes.

9. The method according to claim 8 wherein step (d) comprises annealing a DNA oligomer of a sequence complementary to the specific mRNA sequence or sequences and producing one or more cDNA sequences therefrom with reverse transcriptase.

10. The method according to claim 9 wherein step (e) comprises amplifying the cDNA sequence or sequences by polymerase chain reaction and, in step (f), detecting the presence of the cDNA sequence or sequences comprises quantitating the amount of the cDNA sequence or sequences.

11. The method according to claim 1 wherein, in step (e), the number of copies of the cDNA is amplified in the presence of one or more radiolabeled nucleotides or detectable nucleotide analogs.

12. The method according to claim 10 wherein, in step (e), the polymerase chain reaction is carried out in the presence of one or more radiolabeled nucleotides or detectable nucleotide analogs.

13. The method according to claim 11 wherein, in step (f), when radiolabeled nucleotides are used in step (e), the presence of said cDNA sequence or sequences is detected by directly or indirectly measuring the radioactivity present.

14. The method according to claim 12 wherein, in step (f), when radiolabeled nucleotides are used in step (e), the presence of said cDNA sequence or sequences is detected by directly or indirectly measuring the amount of radioactivity present.

15. The method according to claim 1 wherein, in step (f) the presence of said cDNA sequence or sequences is detected by hybridizing said cDNA sequence or sequences with a radiolabeled DNA probe and measuring the radioactivity that has hybridized to said cDNA sequence or sequences.

16. The method according to claim 10 wherein, in step (f) the presence of said cDNA sequence or sequences is detected by hybridizing said cDNA sequence or sequences with a radiolabeled DNA probe or probes and measuring the radioactivity that has hybridized to said cDNA sequence or sequences.

17. The method according to claim 1 wherein the specific mRNA is mRNA selected from the group of mRNA produced during active infection of cells by HTLV III.

18. The method according to claim 10 wherein the specific mRNA is mRNA selected from the group of mRNA specifically or preferentially produced by cancerous cells.

19. A method for determining the effect of a compound on the presence of a specific mRNA sequence or sequences in cells cultured in vitro which comprises the steps of:
   (a) culturing a first group of the cells in the absence of said compound;
   (b) culturing a second group of the cells in the presence of said compound; and
   (c) separately determining the presence of a specific mRNA sequence or sequences in said first and second groups of the cells according to the method of claim 1.

20. A method for determining the effect of a compound on the presence of a specific mRNA sequence or sequences in cells cultured in vitro which comprises the steps of:
   (a) culturing a first group of the cells in the absence of said compound;
   (b) culturing a second group of the cells in the presence of said compound; and
   (c) separately determining the presence of a specific mRNA sequence or sequences in said first and second groups of the cells according to the method of claim 16.

21. A method for determining the effect of a plurality of compounds on the presence of a specific mRNA sequence or sequences which comprises simultaneously or substantially simultaneously determining said effect for each of said compounds according to claim 19.

22. A method for determining the effect of a plurality of compounds on the presence of a specific mRNA sequence or sequences which comprises simultaneously or substantially simultaneously determining said effect for each of said compounds according to claim 20.

* * * * *

UNITED STATES PATENT AND TRADEMARK OFFICE
CERTIFICATE OF CORRECTION

PATENT NO. : 5,643,730

DATED : July 1, 1997

INVENTOR(S) : Michael J. Banker, Ralph E. Davidson, Dennis A. Pereira,

It is certified that error appears in the above-identified patent and that said Letters Patent is hereby corrected as shown below:

Column 4, line 14, "(50 U/∥l)" should read --(50 U/µl)--;
Column 4, line 29, "HP•7H$_2$O" should read --HPO$_4$•7H$_2$O--;
Column 12, line 47 "Mannhelm" should read --Mannheim--;
Column 12, line 55 "Mannhelm" should read --Mannheim--; and
Column 14, line 49 "Betagert" should read --Betagen--.
Col. 14, line 25, "EXAMPLE2" should read --EXAMPLE 2--.

Signed and Sealed this

Thirtieth Day of September, 1997

*Attest:*

BRUCE LEHMAN

*Attesting Officer*     *Commissioner of Patents and Trademarks*

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
CTTGTAGTGG CTGGCCATCA TGGTCAA                                                           27
```

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
GTGAGCGATG TCAGACAGCT CC                                                                22
```

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
GAAAGCAGAG GCGAAGGCCG GCAT                                                              24
```

( 2 ) INFORMATION FOR SEQ ID NO:4:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

```
GGCACTGTGG CCTGCAGCAT CTCT                                                              24
```

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

```
CGCAGAAGGG GTCCTGGTGA                                                                   20
```

( 2 ) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

```
TTTGCCACCA CCATCTGGCA GCAG                                                              24
```

( 2 ) INFORMATION FOR SEQ ID NO:7:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

```
GCAGGTCGGC TCCTGGAGGT CAAACAT                                                           27
```

( 2 ) INFORMATION FOR SEQ ID NO:8:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

```
CTGGCACAGG AGAGGGGCGG GTG                                          23
```

( 2 ) INFORMATION FOR SEQ ID NO:9:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

```
TTCCCAGTTC TTCCATCTGC TGCCAGATGG                                   30
```

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

```
AGTGCCAACC GCCTCACAGG                                              20
```

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

```
CCTCTCACAC CAGTTCACTC                                              20
```

( 2 ) INFORMATION FOR SEQ ID NO:12:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

```
AGGATATGGT CCTCTTCCA                                               19
```

( 2 ) INFORMATION FOR SEQ ID NO:13:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

```
TGGAAGAGAA CCATATCCT                                               19
```